US012758372B2

(12) United States Patent
Shumaker

(10) Patent No.: US 12,758,372 B2
(45) Date of Patent: Oct. 13, 2026

(54) METHOD FOR DETERMINING PERIODONTAL POCKET DEPTH

(71) Applicant: Nicholas D. Shumaker DDS, MS, PLLC, Fort Collins, CO (US)

(72) Inventor: Nicholas D. Shumaker, Fort Collins, CO (US)

(73) Assignee: Nicholas D. Shumaker DDS, MS, PLLC, Fort Collins, CO (US)

( * ) Notice: Subject to any disclaimer, the term of this patent is extended or adjusted under 35 U.S.C. 154(b) by 230 days.

(21) Appl. No.: 18/826,643

(22) Filed: Sep. 6, 2024

(65) Prior Publication Data

US 2025/0073010 A1 Mar. 6, 2025

Related U.S. Application Data

(60) Provisional application No. 63/536,847, filed on Sep. 6, 2023.

(51) Int. Cl.

| | |
|---|---|
| ***A61C 19/04*** | (2006.01) |
| ***A61B 6/00*** | (2024.01) |
| ***A61B 6/51*** | (2024.01) |
| ***A61C 9/00*** | (2006.01) |
| ***G06T 7/00*** | (2017.01) |
| ***G16H 30/20*** | (2018.01) |

(52) U.S. Cl.

CPC .............. *A61C 19/043* (2013.01); *A61B 6/51* (2024.01); *A61B 6/5247* (2013.01); *A61C 9/0053* (2013.01); *G06T 7/0012* (2013.01); *G16H 30/20* (2018.01); *G06T 2207/10081* (2013.01); *G06T 2207/10116* (2013.01); *G06T 2207/20221* (2013.01); *G06T 2207/30036* (2013.01)

(58) Field of Classification Search

CPC ....... A61C 19/043; A61C 9/0053; A61B 6/51; A61B 6/5247; A61B 6/032; G06T 7/0012; G06T 2207/10081; G06T 2207/10116; G06T 2207/2022; G06T 2207/30036; G16H 30/20

See application file for complete search history.

(56) References Cited

U.S. PATENT DOCUMENTS

| | | | |
|---|---|---|---|
| 4,268,933 | A | 5/1981 | Papas |
| 7,942,672 | B2 | 5/2011 | Kuo |
| 10,123,706 | B2 | 11/2018 | Elbaz et al. |
| 10,201,318 | B2 | 2/2019 | Tsuji et al. |

(Continued)

OTHER PUBLICATIONS

Schmidt et al. Biologic width dimensions—a systematic review. J Clin Periodontol, May 2013, 40(5):493-504.

(Continued)

*Primary Examiner* — Abhishek Sarma

(74) *Attorney, Agent, or Firm* — Craig R. Miles; CR MILES P.C.

(57) ABSTRACT

A broad object of a particular embodiment of the invention can be to provide a method of determining the periodontal pocket depth around a tooth, including: locating the alveolar bone crest of the alveolar bone which supports the tooth to determine an alveolar bone crest location; locating the line where the free gingiva meets the exposed part of the tooth to determine a gumline location; and calculating the periodontal pocket depth using the alveolar bone crest location, the gumline location, and a predetermined biologic width value.

13 Claims, 6 Drawing Sheets

(56) References Cited

U.S. PATENT DOCUMENTS

| | | | | |
|---|---|---|---|---|
| 10,285,635 | B2 | 5/2019 | Motegi | |
| 10,380,212 | B2 | 8/2019 | Elbaz et al. | |
| 10,509,838 | B2 | 12/2019 | Elbaz et al. | |
| 10,528,636 | B2 | 1/2020 | Elbaz et al. | |
| 10,585,958 | B2 | 3/2020 | Elbaz et al. | |
| 10,606,911 | B2 | 3/2020 | Elbaz et al. | |
| 11,045,156 | B2 | 6/2021 | Tsuji et al. | |
| 2014/0234796 | A1* | 8/2014 | Tsuji | A61B 6/032<br>433/29 |
| 2018/0303441 | A1* | 10/2018 | Tsuji | A61B 6/032 |
| 2021/0090255 | A1 | 3/2021 | Kumagai et al. | |
| 2022/0008180 | A1 | 1/2022 | van der Poel et al. | |
| 2022/0189611 | A1 | 6/2022 | Farkash et al. | |
| 2024/0298962 | A1* | 9/2024 | Kwon | A61B 5/4552 |
| 2025/0032087 | A1* | 1/2025 | Jokerst | A61B 8/0833 |

OTHER PUBLICATIONS

Vacek et al. The Dimensions of the Human Dentogingival Junction. Int J Periodontics Restorative Dent, Apr. 1994, 14(2):154-165.

De Vico et al. A novel workflow for computer guided implant surgery matching digital dental casts and CBCT scan. Oral & Implantology, Nov. 2016, 9(1):33-48.

Gargiulo et al. Dimensions and Relations of the Dentogingival Junction in Humans. The Journal of Periodontology, Jul. 1961, 32(3):261-267.

Chung et al. Periodontal probing on digital images compared to clinical measurements in periodontitis patients. Sci Rep, Jan. 2022, 12(1):1616.

Van Der Velden et al. The influence of probing force on the reproducibility of pocket depth measurements. J Clin Periodontol, Oct. 1980, 7(5):414-20.

Fowler et al. Histologic probe position in treated and untreated human periodontal tissues. J Clin Periodontol, Sep. 1982, 9(5):373-85.

Armitage et al. Microscopic evaluation of clinical measurements of connective tissue attachment levels. J Clin Periodontol, Aug. 1977, 4(3): 173-90.

Van Der Zee et al. Marking width, calibration from tip and tine diameter of periodontal probes. J Clin Periodontol, Aug. 1991, 18(7):516-20.

* cited by examiner

METHOD FOR DETERMINING PERIODONTAL POCKET DEPTH

I. SUMMARY OF THE INVENTION

A broad object of a particular embodiment of the invention can be to provide a method of determining the periodontal pocket depth around a tooth, including: locating the alveolar bone crest of the alveolar bone which supports the tooth to determine an alveolar bone crest location; locating the line where the free gingiva meets the exposed part of the tooth to determine a gumline location; and calculating the periodontal pocket depth using the alveolar bone crest location, the gumline location, and a predetermined biologic width value.

Another broad object of a particular embodiment of the invention can be to provide a program code executable to calculate the periodontal pocket depth from an alveolar bone crest location, a gumline location, and a predetermined biologic width value.

Naturally, further objects of the invention are disclosed throughout other areas of the specification, drawings, images, and claims.

II. BRIEF DESCRIPTION OF THE DRAWINGS

III. DETAILED DESCRIPTION OF THE PREFERRED EMBODIMENTS

Figure 1:
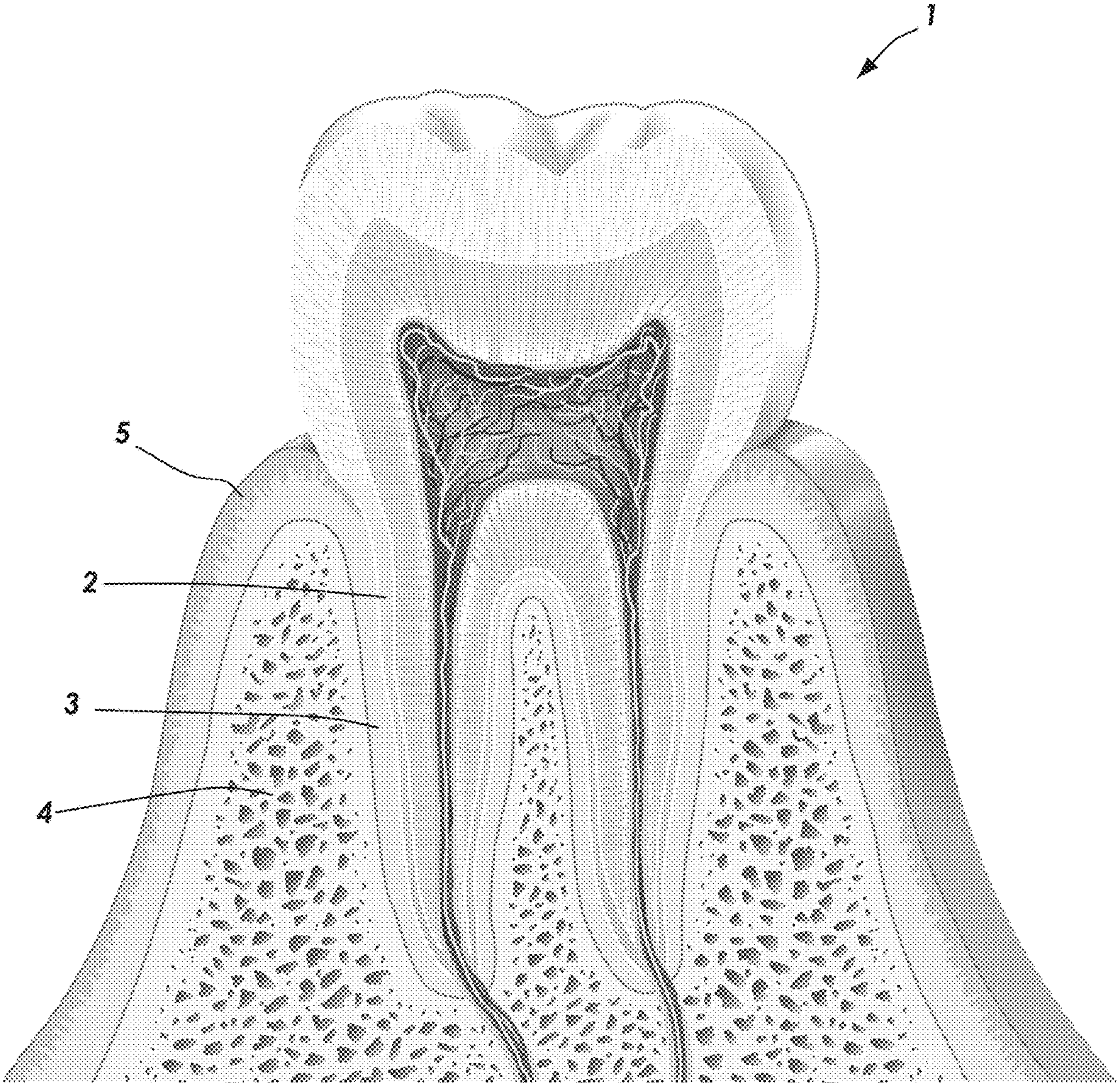
FIG. 1 is an illustration of exemplary tooth anatomy.

Now referring primarily to FIG. 1, briefly, the teeth (1) are supported by the periodontium which comprises specialized tissues and in particular, cementum (2), the periodontal ligament (3), alveolar bone (4), and gingival tissue (5). Regarding the latter, the gingiva (or gums) (5) surrounds the teeth (1) and the marginal parts of the alveolar bone (4), forming a collar or cuff around each tooth (1).

Figure 2:
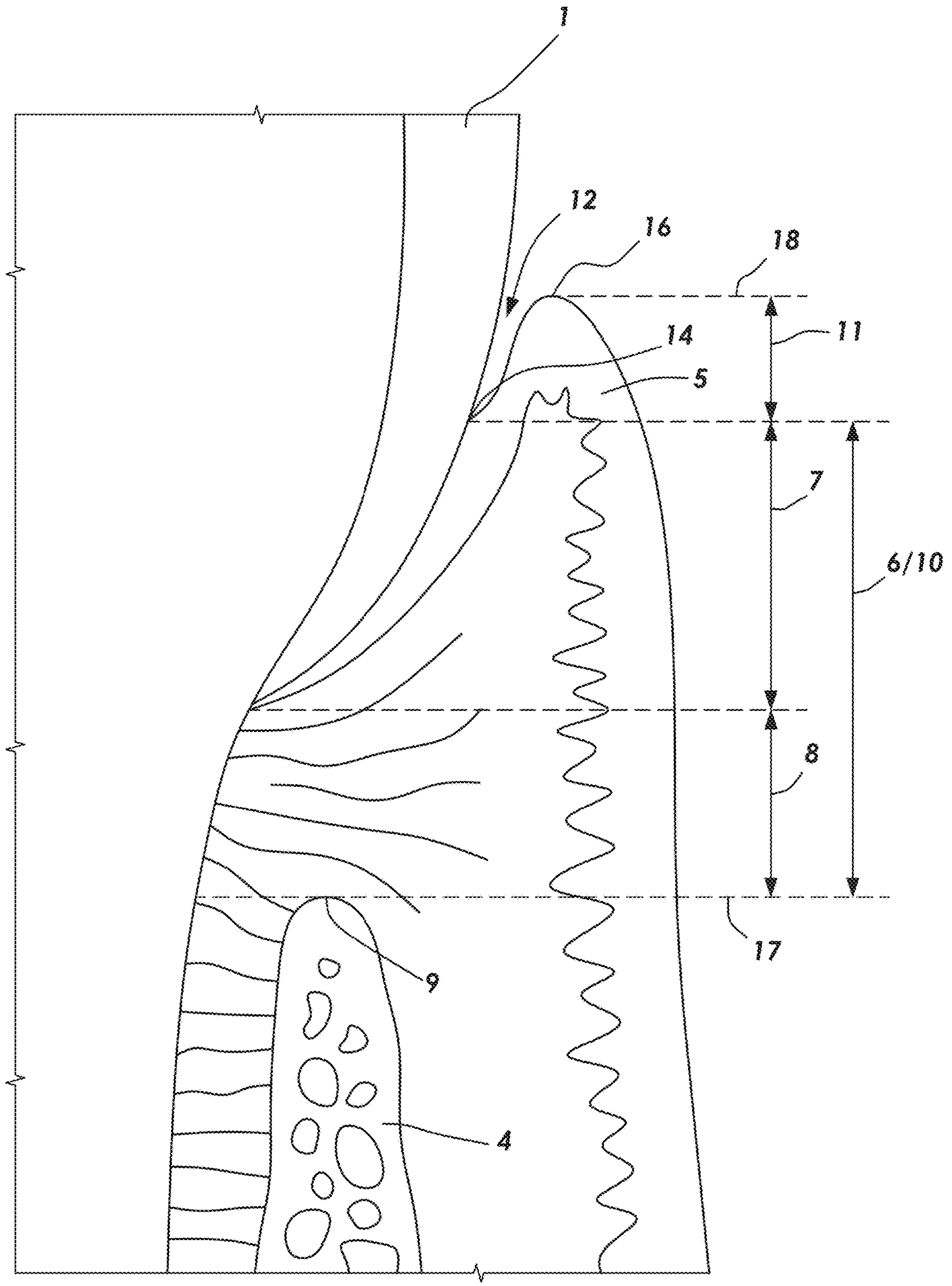
FIG. 2 is an illustration of exemplary tooth anatomy, specifically showing the junctional epithelium and connective tissue that together provide the biologic width.

Now referring primarily to FIG. 2, the gingiva (5) includes the attached gingiva (6), which is physically and firmly attached to the cementum (2) and alveolar bone (4) by means of junctional epithelium (7) and connective tissue (8). In more detail, the junctional epithelium (7) is the unkeratinized, highly permeable epithelium which is coronal to the connective tissue (8) and forms the epithelial attachment to the surface of the tooth (1). The connective tissue (8) is apical to the junctional epithelium (7) and ends at the alveolar bone crest (9); connective tissue fibers insert directly into the cementum (2) to attach the gingiva (5) to the tooth (1) and form the connective tissue attachment.

Again referring primarily to FIG. 2, the gingival attachment to the tooth (1), termed the "biologic width" (10) (also called the physiologic dentogingival junction or supracrestal periodontal attachment), is defined as the combined height of the junctional epithelium (7) and the connective tissue (8), or more generally, the dimension of the soft tissue which is attached to the portion of the tooth (1) coronal to the alveolar bone crest (9). The term biologic width (10) is based on the work of Gargiulo et al. who describes the dimensions and relationships of the dentogingival junction in humans (Gargiulo A W, Wentz F M, Orban B. Dimensions and relations of the dentogingival junction in humans. *The Journal of Periodontology*. 1961 July; 32 (3): 261-7). The biologic width (10) provides the natural seal that develops around a tooth (1) to protect against invasion from bacteria and other foreign materials.

Again referring primarily to FIG. 2, the gingiva (5) further includes the free gingiva (11), which disposes close to the surface of the tooth (1) but is not attached to the tooth (1). A small invagination or sulcus is formed between the tooth (1) and the free gingiva (11); thus, a shallow groove termed the gingival sulcus (12) surrounds each tooth (1), lined by tooth structure on one side and sulcular epithelium on the other side.

Figure 3:
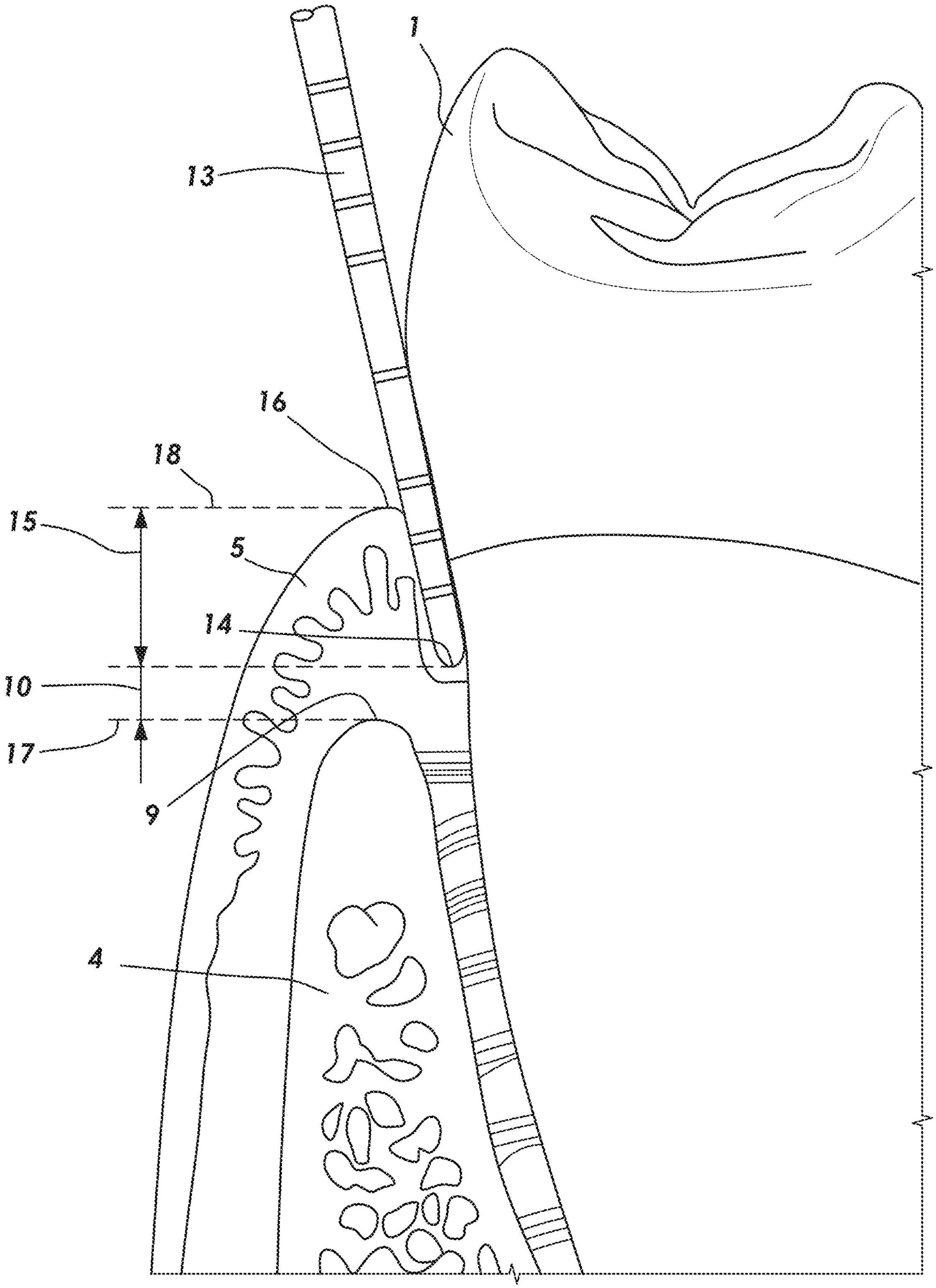
FIG. 3 is an illustration of conventional periodontal probing which is used to determine periodontal pocket depth.

Now referring primarily to FIG. 3, a periodontal pocket is a pathologically deepened gingival sulcus (12) due to gingival recession and in particular, apical migration of the junctional epithelium (7). Periodontal charting (also known as periodontal probing) is a dental procedure, typically performed by a dentist or dental hygienist, that involves manually measuring the depth of the gingival sulcus (12) and/or of the pockets around each tooth (1) by gently inserting a graduated periodontal probe (13) until resistance is encountered, whereby this resistance is taken to be the base (14) of the gingival sulcus (12). In this way, the periodontal probing depth or periodontal pocket depth (15), which is the distance from the gumline (16) to the base (14) of the gingival sulcus (12), has conventionally been measured and used to evaluate the health of the gums (5) and the alveolar bone (4) surrounding the teeth (1). In the periodontally normal/healthy individual, the gingival sulcus (12) is about 1-3 mm deep in humans and dogs and about 0.5-1 mm deep in cats. An increased periodontal probing depth or periodontal pocket depth (15) can indicate a greater degree of gum recession or bone loss, which can be a sign of periodontal disease.

Notably, conventional periodontal probing can be time-consuming and/or uncomfortable for the patient. Additionally, conventional periodontal probing can be inaccurate, due to both intra-examiner and inter-examiner variability which may result from several factors, including variations in probing force (van der Velden U, de Vries J H. The influence of probing force on the reproducibility of pocket depth measurements. *J Clin Periodontol.* 1980 October; 7 (5): 414-20), angle/position/tooth location (Fowler C, Garrett S, Crigger M, Egelberg J. Histologic probe position in treated and untreated human periodontal tissues. *J Clin Periodontol.* 1982 September; 9 (5): 373-85), amount of inflammation present (Armitage G C, Svanberg G K, Löe H. Microscopic evaluation of clinical measurements of connective tissue attachment levels. *J Clin Periodontol.* 1977 August; 4 (3): 173-90), and periodontal probe design/type (Van der Zee E, Davies E H, Newman H N. Marking width, calibration from tip and tine diameter of periodontal probes. *J Clin Periodontol.* 1991 August; 18 (7): 516-20).

As an answer to the drawbacks and/or shortcomings of conventional periodontal probing, disclosed herein is an alternative thereto which allows the periodontal pocket depth (15) around a tooth (1) (whether natural, real, artificial, fake, prosthetic, a dental implant, etc.) to be determined without the use of a periodontal probe (13), whereby the present method includes locating the alveolar bone crest (9) of the alveolar bone (4) which supports the tooth (1) to determine an alveolar bone crest location (17) (or level); locating the line where the free gingiva (11) meets the exposed part of the tooth (1) to determine a gumline location (18) (or level); and calculating the periodontal pocket depth (15) using the alveolar bone crest location (17), the gumline location (18), and a predetermined biologic width (10) value. Following the determination of the periodontal pocket depth (15) around each tooth (1) in a patient's mouth, a complete "virtual" periodontal chart can be generated. Advantageously, this "virtual periodontal charting" method can be relatively quick, efficient, and minimally invasive, particularly in relation to conventional periodontal probing. Further, the inventive method may "standardize" periodontal pocket depth (15) determination, which may correspondingly improve accuracy and reduce error(s) relative to conventional periodontal probing.

Figure 4:
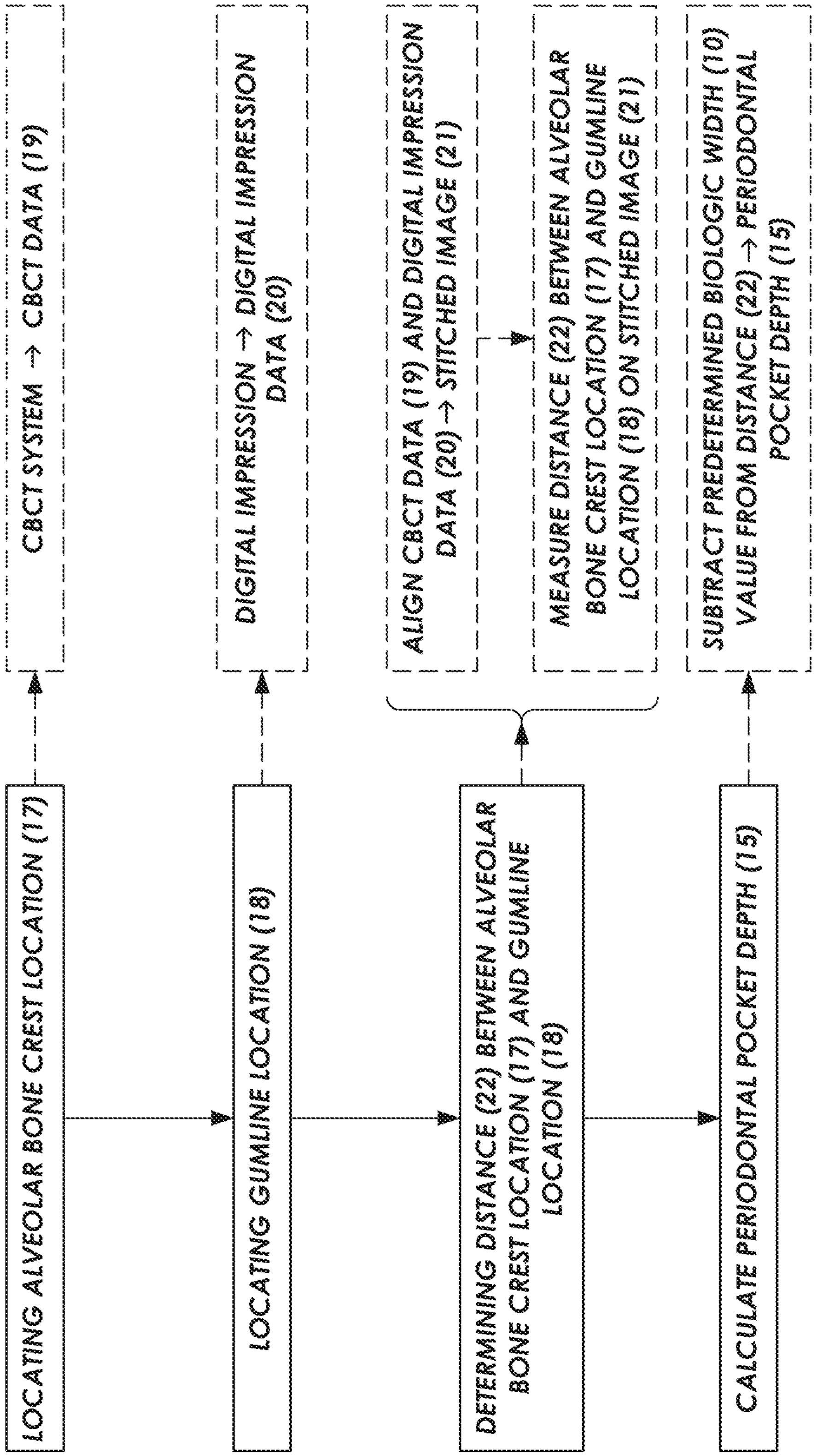
FIG. 4 is a flow chart of a particular embodiment of the present inventive method for determining periodontal pocket depth.

Now referring primarily to FIG. 4, the present method of determining the periodontal pocket depth (15) around a tooth (1) includes locating the alveolar bone crest (9) of the alveolar bone (4) which supports the tooth (1) to determine an alveolar bone crest location (17), whereby the step of locating the alveolar bone crest (9) can be done by any suitable method, such as via full mouth x-rays (FMX), panoramic x-rays (PANO), three-dimensional (3D) X-rays, or the like.

Figure 5A:
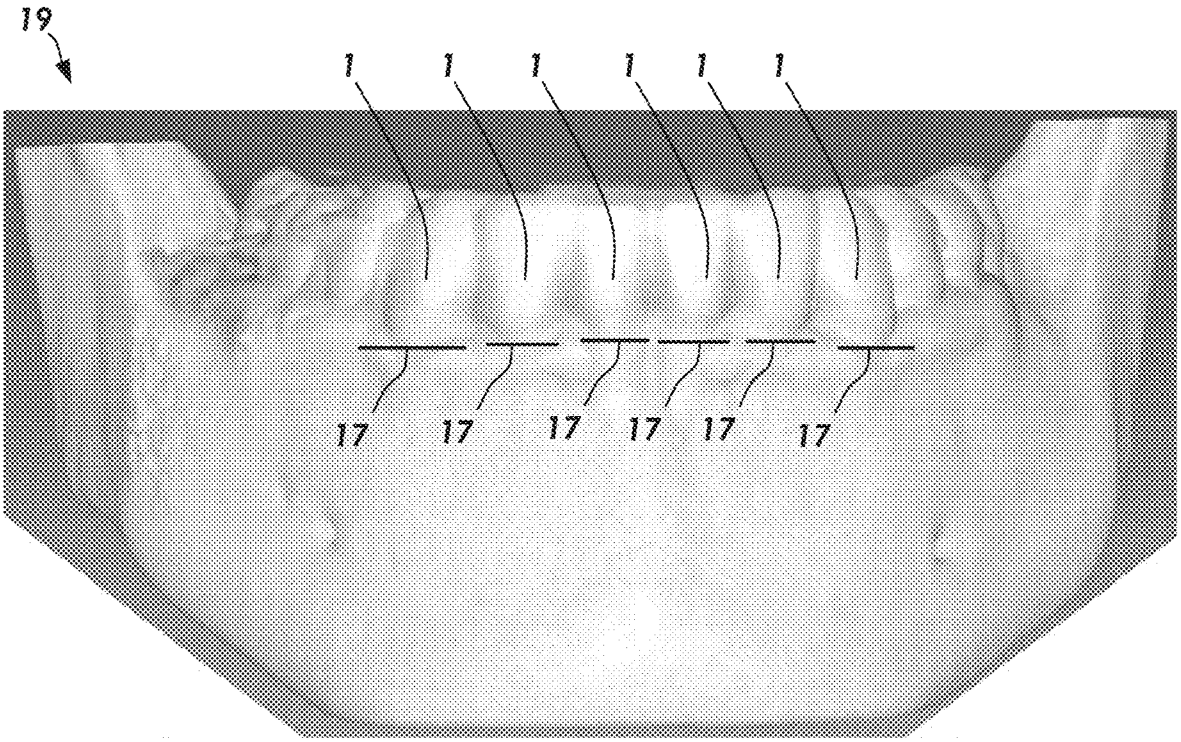
FIG. 5A shows CBCT scan data annotated with alveolar bone crest locations for the facial surfaces of a plurality of teeth.

Now referring primarily to FIG. 5A, as but one illustrative example, the alveolar bone crest (9) of the alveolar bone (4) which supports the tooth (1) can be located via a cone beam computed tomography (CBCT) system which can rotate around the patient, capturing multiple X-ray images (i.e. data) from different angles using a cone-shaped X-ray beam. The images can then be reconstructed to produce a three-dimensional (3D) image of bones, soft tissues, and nerves in an area of interest; for example, a CBCT system can produce CBCT data (19) (which may be in the form of a Digital Imaging and Communications in Medicine (.DICOM or .DCM) file or the like comprising a 3D image of the teeth (1), the oral and maxillofacial region (mouth, jaw, and neck), etc. Compared to traditional CT scans, CBCT scans may be quicker, produce less radiation exposure to the patient, and offer high-resolution images with excellent detail.

Now referring primarily to FIG. 4, the present method of determining the periodontal pocket depth (15) around a tooth (1) further includes locating the line where the free gingiva (11) meets the exposed part of the tooth (1) to determine a gumline location (18). Of note, as used herein, gumline (16) can be synonymous with free gingival margin and/or crest of the free gingiva. This step of locating the gumline (16) can be done by any suitable method; however, a method which produces images (i.e. data) which can be merged with CBCT data (19) may be preferable.

Figure 5B:
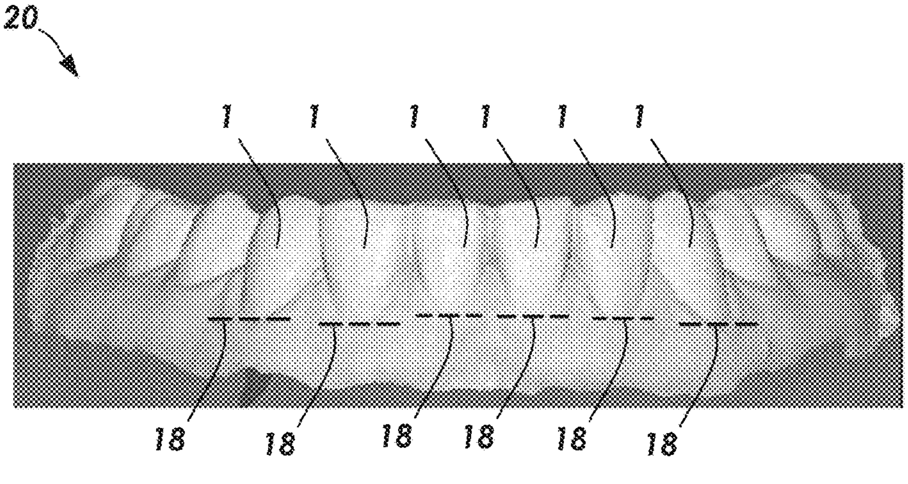
FIG. 5B shows digital impression data annotated with gumline locations for the facial surfaces of the same plurality of teeth shown in FIG. 5A.

With reference to FIG. 5B as but one illustrative example, the gumline (16) can be located using dental scans taken with three-dimensional (3D) scanning technology, termed digital impressions, which provide computer-generated replicas of dental anatomy and soft tissues. Digital impression data (20) is typically created using an intraoral scanner that takes digital images of the teeth (1) and surrounding tissues; these images can then be used to create a highly accurate 3D digital model of the teeth (1) and gums (5), which may take the form of a Standard Triangulation Language (.STL) file, a .PLY file, an .OBJ file, or the like. Exemplary intraoral scanners include, but are not limited to, the iTero™ Digital Impression Scanner from Align Technology, the TRIOS® Intraoral Scanner from 3Shape, the Primescan intraoral scanner from Dentsply Sirona, the Medit intraoral scanner from Medit.

Figure 5C:
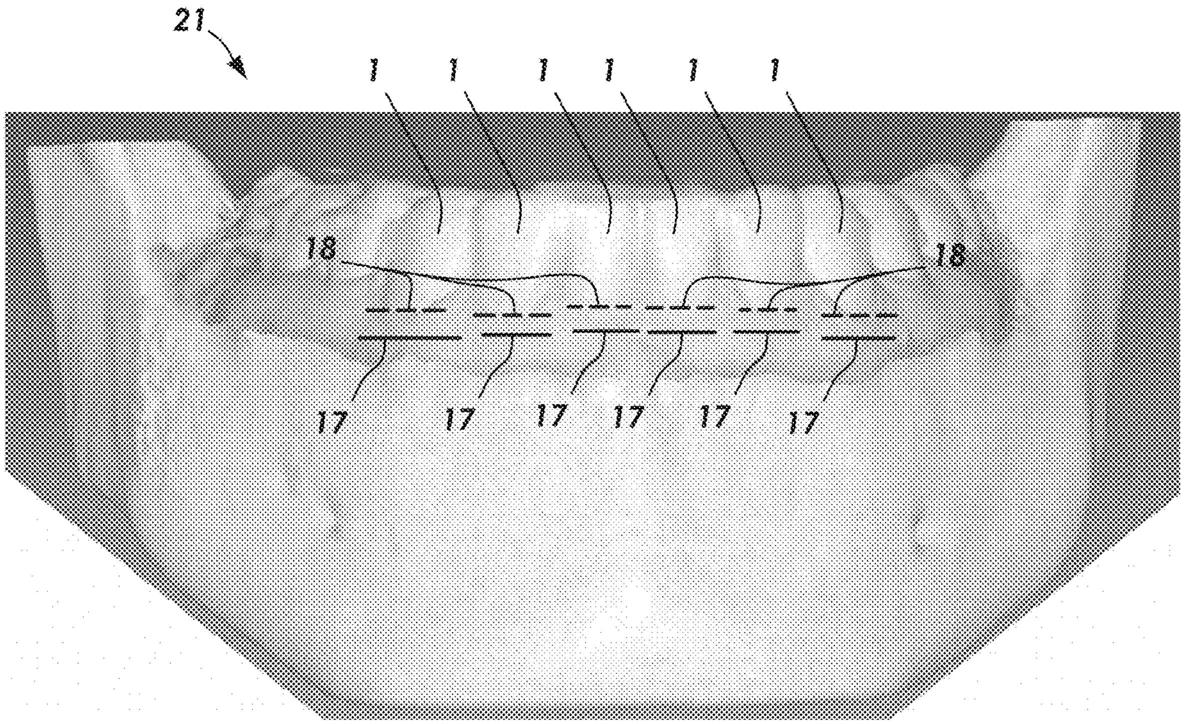
FIG. 5C shows a "stitched image" derived from stitching together the CBCT scan data shown in FIG. 5A and the digital impression data shown in FIG. 5C, whereby the image is annotated with the corresponding alveolar bone crest locations and gumline locations.

Now referring primarily to FIG. 5C, subsequent to the acquisition of the CBCT data (19) and the digital impression data (20), the images can be precisely merged (or stitched together or matched or superimposed) to provide a "stitched image" (21) via a process that involves registration and integration of the two data sets (19) (20). Briefly, the CBCT data (19) and the digital impression data (20) are aligned and overlaid in a common coordinate system, such as by point-based, intensity-based, or feature-based registration. Corresponding landmarks or fiducial markers are identified in both the CBCT data (19) and digital impression data (20), whereby these landmarks serve as reference points for aligning the two data sets (19) (20) accurately. Using the identified landmarks, a transformation is performed to align the CBCT data (19) and digital impression data (20) to provide the stitched image (21), whereby the transformation accounts for any differences in position, orientation, and scale between the two data sets (19) (20).

Subsequently, the stitched image (21) can provide (i) the alveolar bone crest location (17) for one or more teeth (1) and (ii) the gumline location (18) of said one or more teeth (1). Thus, the distance (22) or spatial relationship between the two (17) (18) can be determined, such as via measuring.

As per the present invention, the method of determining the periodontal pocket depth (15) around a tooth (1) further includes calculating the periodontal pocket depth (15) using the alveolar bone crest location (17), the gumline location (18), and a predetermined biologic width (10) value, whereby as used herein, the term "predetermined" can mean decided in advance. As described above, the biologic width (10), which provides the natural seal that develops around a tooth (1), is the combined height of the junctional epithelium (7) and the connective tissue (8). Numerous studies which are found in the published literature have measured biologic width (10), with a few examples as follows.

Gargiulo et al. obtained measurements from human autopsy specimens and in particular, 287 individual teeth and their respective dentogingival components from 30 jaws. He concludes that "there is a somewhat definite proportional dimensional relation between the dentogingival junction and the other supporting tissues of the tooth," finding that the average biologic width (10) is 2.04 millimeters (mm), from a combined 0.97 mm of junctional epithelium (7) and 1.07 mm of connective tissue (8), and the average depth of the gingival sulcus (12) is 0.69 mm. Of note, Gargiulo et al. found that the connective tissue (8) measurement is the most constant, and the junctional epithelium (7) measurement is the most variable.

Vacek et al. examined the naturally occurring dimensions of the dentogingival junction in ten adult human cadaver jaws and found that the mean biologic width (10) is 1.91 mm, from a combined 1.14±0.49 mm of junctional epithelium (7) and 0.77±0.32 mm of connective tissue (8), and the average depth of the gingival sulcus (12) is 1.34±0.84 mm (Vacek J S, Gher M E, Assad D A, Richardson A C, Giambarresi L I. The dimensions of the human dentogingival junction. *Int J Periodontics Restorative Dent.* 1994 April; 14 (2): 154-65). Vacek et al. also found that (i) there were no significant differences in the biologic width (10) measurements between the buccal, lingual, mesial, and distal tooth surfaces, (ii) the posterior teeth showed a significantly greater (P<0.004) biologic width (10) than the anterior teeth, and (iii) there was no correlation between loss of attachment (the distance from the cementoenamel junction to the most coronal extent of the connective tissue (8)) and biologic width (10).

Schmidt et al. found that the mean values of the biologic width (10) obtained from two meta-analyses ranged from 2.15 to 2.30 mm (Schmidt J C, Sahrmann P, Weiger R, Schmidlin P R, Walter C. Biologic width dimensions—a systematic review. *J Clin Periodontol.* 2013 May; 40 (5): 493-504).

It is herein noted that the above three studies are exemplary only, and any predetermined biologic width (10) value, such as from the published literature which provides biologic width (10) data, can be used with the present invention.

Figure 5D:
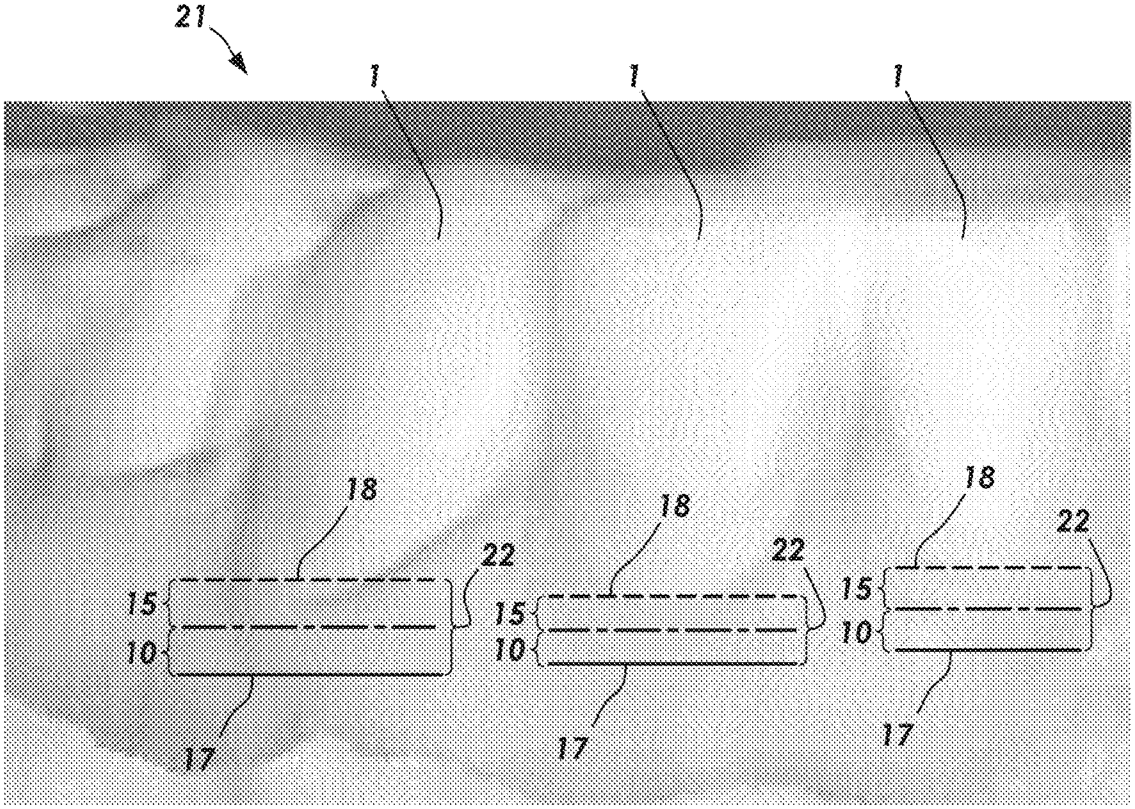
FIG. 5D is an enlarged view of a portion of the stitched image shown in FIG. 5C further annotated to show (i) biologic widths derived from a predetermined biologic width value and (ii) periodontal pocket depths of three teeth.

As to particular embodiments, to calculate the periodontal pocket depth (15) for a tooth (1), the predetermined biologic width (10) value can be subtracted from the distance (22) between the alveolar bone crest location (17) and the gumline location (18) obtained from the stitched image (21) of said tooth (1). Now, referring primarily to FIG. 5D as an example, (i) proximate the middle (or center) of the tooth (1), the distance (22) between the alveolar bone crest location (17) and the gumline location (18) can be about 4 mm, and (ii) proximate the sides (mesial and distal) of the tooth (1), the distance (22) between the alveolar bone crest location (17) and the gumline location (18) can be about 5 mm. By subtracting a biologic width (10) value of about 2 mm (for example as derived from Gargiulo et al.) from each site, the periodontal pocket depth (15) (*i*) proximate the middle of the tooth (1) can be about 2 mm, and (ii) proximate the sides (mesial and distal) of the tooth (1) can be about 3 mm, for a "shorthand" periodontal pocket depth (15) of 3-2-3.

As to particular embodiments, the present invention can further include a program code and/or application and/or software (such as is contained in a non-transitory computer readable medium communicatively coupled to a processor) executable to select a tooth (1) in a plurality of scanned teeth (1), determine the alveolar bone crest location (17) for the selected tooth (1) (such as from a stitched image (21) of said tooth (1)), determine the gumline location (18) for the selected tooth (1) (such as from the stitched image (21) of said tooth (1)), determine the distance (22) between the alveolar bone crest location (17) and the gumline location (18) (such as from the stitched image (21) for the selected tooth (1)), and generate a periodontal pocket depth (15) for the selected tooth (1) using a predetermined biologic width (10) value. Generating the periodontal pocket depth (15) can include calculating, such as with the use of an algorithm, the periodontal pocket depth (15) using the predetermined biologic width (10) value. Calculating the periodontal pocket depth (15) can include subtracting the predetermined biologic width (10) value from the distance (22) between the alveolar bone crest location (17) and the gumline location (18).

As to particular embodiments, the program code can further be executable to record the periodontal pocket depth (15) for the selected tooth (1).

As to particular embodiments, the program code can further be executable to display on a display surface the periodontal pocket depth (15) for the selected tooth (1), such as in measurement units.

As to particular embodiments, the program code can further be executable to identify a selected tooth (1) by its location, such as by its number (for example, 3, 11, 26, etc.) and/or name (for example, first molar, cuspid, lateral incisor, etc.).

As to particular embodiments, the program code can further be executable to associate a specific predetermined biologic width (10) value with an identified tooth (1) based on its location. For example, as derived from Vacek et al., a biologic width (10) value of about 1.75 mm can be associated with a tooth (1) identified as anterior, and a biologic width (10) value of about 2.08 mm can be associated with a tooth (1) identified as a molar.

As to particular embodiments, the program code can further be executable to determine the periodontal health of a patient and specifically, whether the periodontal pocket depth (15) generated for a selected tooth (1) is considered (i) normal/healthy, (ii) indicative of mild periodontitis, (iii) indicative of moderate periodontitis, or (iv) indicative of advanced periodontitis.

As to particular embodiments, the program code can further be executable to flag a generated periodontal pocket depth (15) that is considered (i) indicative of mild periodontitis, (ii) indicative of moderate periodontitis, or (iii) indicative of advanced periodontitis.

As to particular embodiments, the program code can further be executable to suggest a treatment plan for a generated periodontal pocket depth (15) that is considered (i) indicative of mild periodontitis, (ii) indicative of moderate periodontitis, or (iii) indicative of advanced periodontitis.

As to particular embodiments, the program code can further be executable to stitch the CBCT data (19) and the digital impression data (20).

As to particular embodiments, the program code can further be executable to receive CBCT data (19) from a CBCT system, and receive digital impression data (20) from an intraoral scanner.

As can be easily understood from the foregoing, the basic concepts of the present invention may be embodied in a variety of ways. The invention involves numerous and varied embodiments of a method for determining a periodontal pocket depth of a tooth and executable programs for such a method.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "location" should be understood to encompass disclosure of the act of "locating"—whether explicitly discussed or not—and, conversely, were there effectively disclosure of the act of "locating," such a disclosure should be understood to encompass disclosure of a "locator" and even a "means for locating." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the methods for determining a periodontal pocket depth of a tooth and executable programs for such a method herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application, if any, provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method of determining the periodontal pocket depth around a tooth, comprising:

locating the alveolar bone crest of the alveolar bone which supports said tooth to determine an alveolar bone crest location;

wherein said alveolar bone crest location is determined via cone beam computed tomography data;

locating the line where the free gingiva meets the exposed part of said tooth to determine a gumline location; and wherein said gumline location is determined via digital impression data; and where in the distance between said alveolar bone crest location and said gumline location is determined via a stitched image in which said cone beam computed tomography data and said digital impression data are merged; and executing a program code contained in a non-transitory computer readable medium communicatively coupled to a processor to:

calculating calculate said periodontal pocket depth for said tooth using said alveolar bone crest location, said gumline location, and a predetermined biologic width value to generate a calculated periodontal pocket depth;

determine whether said calculated periodontal pocket depth is considered (i) normal/healthy, (ii) indicative of mild periodontitis, (iii) indicative of moderate periodontitis, or (iv) indicative of advanced periodontitis;

flag said calculated periodontal pocket depth that is considered (i) indicative of mild periodontitis, (ii) indicative of moderate periodontitis, or (iii) indicative of advanced periodontitis; and suggest a treatment plan for said calculated periodontal pocket depth that is considered (i) indicative of mild periodontitis, (ii) indicative of moderate periodontitis, or (iii) indicative of advanced periodontitis.

2. The method of claim 1, wherein said periodontal pocket depth is determined without the use of a periodontal probe.

3. The method of claim 1, wherein said cone beam computed tomography data is in the form of a Digital Imaging and Communications in Medicine (.DICOM or .DCM) file.

4. The method of claim 1, wherein said digital impression data is created via an intraoral scanner.

5. The method of claim 1, wherein said digital impression data is in the form of a Standard Triangulation Language (.STL) file, a .PLY file, or an .OBJ file.

6. The method of claim 1, wherein said periodontal pocket depth is calculated by subtracting said predetermined biologic width value from said distance between said alveolar bone crest location and said gumline location.

7. The method of claim 1, wherein said peredetermined biologic width value is derived from biologic width data contained in the published literature.

8. The method of claim 1, wherein said predetermined biologic width value is about 2 millimeters.

9. The method of claim 1, said program code executable to:

record said periodontal pocket depth for said selected tooth; and display said periodontal pocket depth for said selected tooth on a display surface.

10. The method of claim 1, said program code executable to:

identify said selected tooth by its location to provide an identified tooth; and associate a specific said predetermined biologic width value with said identified tooth based on its location.

11. The method of claim 1, said program code executable to determine the periodontal health of a patient.

12. The method of claim 1, said program code executable to generate a virtual periodontal chart following determination of said periodontal pocket depth around said tooth.

13. The method of claim 12, further comprising using said virtual periodontal chart in place of conventional periodontal probing to determine the periodontal health of a patient.

* * * * *